(12) United States Patent
Van Wyck et al.

(10) Patent No.: US 12,181,458 B2
(45) Date of Patent: Dec. 31, 2024

(54) FIBER-OPTIC BUNDLE FOR IN-SITU SPECTRAL SENSOR, SPECTRAL SENSOR AND METHOD OF MAKING AND USING THE SAME

(71) Applicant: LandScan LLC, San Luis Obispo, CA (US)

(72) Inventors: Neal Edward Van Wyck, Jericho, VT (US); Darren C. Nolet, Hartland, VT (US); Maxwell S. Farrington, Stockbridge, VT (US); Stephen P. Farrington, Stockbridge, VT (US); Daniel James Rooney, Charleston, SC (US)

(73) Assignee: LandScan LLC, Davis, CA (US)

( * ) Notice: Subject to any disclaimer, the term of this patent is extended or adjusted under 35 U.S.C. 154(b) by 158 days.

(21) Appl. No.: 18/086,219

(22) Filed: Dec. 21, 2022

(65) Prior Publication Data
US 2024/0210374 A1 Jun. 27, 2024

(51) Int. Cl.
G02B 6/04 (2006.01)
G01J 3/02 (2006.01)
G01J 3/10 (2006.01)
G01N 33/24 (2006.01)

(52) U.S. Cl.
CPC ............ *G01N 33/24* (2013.01); *G01J 3/0208* (2013.01); *G01J 3/0218* (2013.01); *G01J 3/108* (2013.01); *G01N 33/245* (2024.05)

(58) Field of Classification Search
CPC ..... G01N 33/24; G01N 33/245; G01J 3/0208; G01J 3/0218; G01J 3/108; G02B 6/04; G02B 6/10
See application file for complete search history.

(56) References Cited

U.S. PATENT DOCUMENTS

| | | | |
|---|---|---|---|
| 5,754,715 A | 5/1998 | Melling | |
| 6,243,520 B1 * | 6/2001 | Goldman | G02B 6/06 385/115 |
| 2006/0051036 A1 | 3/2006 | Treado et al. | |
| 2009/0257046 A1 | 10/2009 | Dean et al. | |
| 2014/0371602 A1 * | 12/2014 | Ito | A61B 5/0075 600/478 |

OTHER PUBLICATIONS

THORLABS webpage. Fiber Optic Reflection/Backscatter Probe Bundles. https://www.thorlabs.com/newgrouppage9.cfm?objectgroup_id=7794 (Last viewed on Dec. 21, 2022).

(Continued)

*Primary Examiner* — Abdullahi Nur
(74) *Attorney, Agent, or Firm* — Downs Rachlin Martin PLLC (57) ABSTRACT

Fiber-optic bundles for infrared spectral analysis of media. The fiber-optic bundles can be used in infrared probes configured to be inserted in media for in-situ characterization of the media. The fiber-optic bundles can include a plurality of optical fibers arranged in a spatial pattern at a sampling end of the bundle to improve a signal of infrared spectral measurements. In-situ probes of the present disclosure can be used for precision farming practices to improve soil health and increase crop yields.

20 Claims, 8 Drawing Sheets

(56) References Cited

OTHER PUBLICATIONS

Ocean Insight webpage. Visible-NIR Reflection/Backscatter Probes. https://www.oceaninsight.com/products/fibers-and-probes/probes/reflectionbackscatter-probes/vis-nir-reflectionbackscatter-probes/ (Last viewed on Dec. 21, 2022).

Ocean Insight webpage. UV-Visible Bifurcated Optical Fiber Assembly. https://www.oceaninsight.com/products/fibers-and-probes/fibers/bifurcated-fibers/uv-vis-bifurcated-fiber/ (Last viewed on Dec. 21, 2022).

THORLABS webpage. Fiber Bundle Adapters for OSL2, OSL2IR, and Former OSL1 Fiber Light Sources. https://www.thorlabs.com/newgrouppage9.cfm?objectgroup_id=7510 (Last viewed on Dec. 21, 2022).

THORLABS webpage. Bifurcated Fiber Bundles 19 Fibers. https://www.thorlabs.com/newgrouppage9.cfm?objectgroup_id=8037 (Last viewed on Dec. 21, 2022).

\* cited by examiner

FIBER-OPTIC BUNDLE FOR IN-SITU SPECTRAL SENSOR, SPECTRAL SENSOR AND METHOD OF MAKING AND USING THE SAME

FIELD OF THE DISCLOSURE

The present disclosure relates to the field of spectrometry. More specifically, it relates to fiber-optic bundles for use in an in-situ spectral probe, especially for spectral sensing of components of soil and other media in which the probe is positioned.

BACKGROUND

The agricultural sector accounts for a substantial portion of total greenhouse gas emissions. However, certain agricultural practices, variously labeled as sustainable agriculture, climate smart farming, regenerative agriculture, etc., also have the potential to return atmospheric carbon to the soil in relatively persistent form. Agricultural technology or agtech reduces greenhouse gas emissions, improves crop yields, and increases soil carbon stores. One specific application of agtech is the use of sensors to determine soil health through the measurement of water, organic carbon, and nutrient content in the soil as well as soil structure. In-situ soil probes equipped with spectral sensors can be used to determine the level and spatial distribution of nutrients such as nitrogen, phosphorus, and potassium in the soil, and quantify soil organic carbon (SOC). The measurement data is used to optimize the level of water and fertilizer applied to crops and to verify practices that capture carbon in the soil.

Various spectral sensing techniques are reliable testing methods for determining the constituents of a sample. In a laboratory-based process, test samples are collected in the field, placed in appropriate sample containers and cataloged for future analysis. In a field-based process, spectral data is collected in the field by a probe, such as a soil probe, that is equipped with spectral sensors. With either the lab or field based process, a light source is utilized to illuminate the sample. The sample absorbs, transmits, or reflects the incident light according to, among other things, different chemical bonds which may be present among the constituents of the sample. At least one spectrometer receives light reflected or emitted from the sample and measures the intensity of the reflected or emitted light in each of several wavelength bands. Quantities of various compounds present in the sample and mineral composition of soil grains may be determined from the spectral analysis. In soil and/or earth related fields including geology, agriculture, and environmental contamination spectral sensing can be useful. For example, spectral sensing can be used in precision farming to measure the amount of nutrients in the soil and determine soil health, which can be used to modify management practices to increase crop yield and reduce greenhouse gas emissions.

SUMMARY OF THE DISCLOSURE

In one implementation, the present disclosure is directed to a fiber-optic bundle. The fiber-optic bundles includes a sampling end; and a plurality of optical fibers that include a first receiver fiber; a second receiver fiber; and a plurality of illumination fibers arranged in an asymmetric pattern at the sampling end, wherein the asymmetric pattern is designed and configured to provide a first illumination intensity incident on the first receiver and a second illumination intensity incident on the second receiver fiber, wherein the first illumination intensity is greater than the second illumination intensity.

In another implementation, the present disclosure is directed to a method of manufacturing a fiber-optic bundle. The method includes obtaining a plurality of optical fibers that include a first receiver fiber, a second receiver fiber, and a plurality of illumination fibers; and arranging the plurality of illumination fibers in an asymmetric pattern at a sampling end of the fiber-optic bundle, wherein the asymmetric pattern is designed and configured to provide a first illumination intensity incident on the first receiver and a second illumination intensity incident on the second receiver fiber, wherein the first illumination intensity is greater than the second illumination intensity.

BRIEF DESCRIPTION OF THE DRAWINGS

For the purpose of illustrating the disclosure, the drawings show aspects of one or more embodiments of the disclosure. However, it should be understood that the present disclosure is not limited to the precise arrangements and instrumentalities shown in the drawings, wherein.

DETAILED DESCRIPTION

Throughout the present disclosure, unless otherwise specified, the terms "about" and "substantially," when used with a corresponding numeric value may refer to ±20% of the numeric value, or may refer to ±10% of the numeric value, or may refer to ±5% of the numeric value, or may refer to ±2% of the numeric value. In some examples, the term "about" may mean the numeric value itself.

Figure 1:
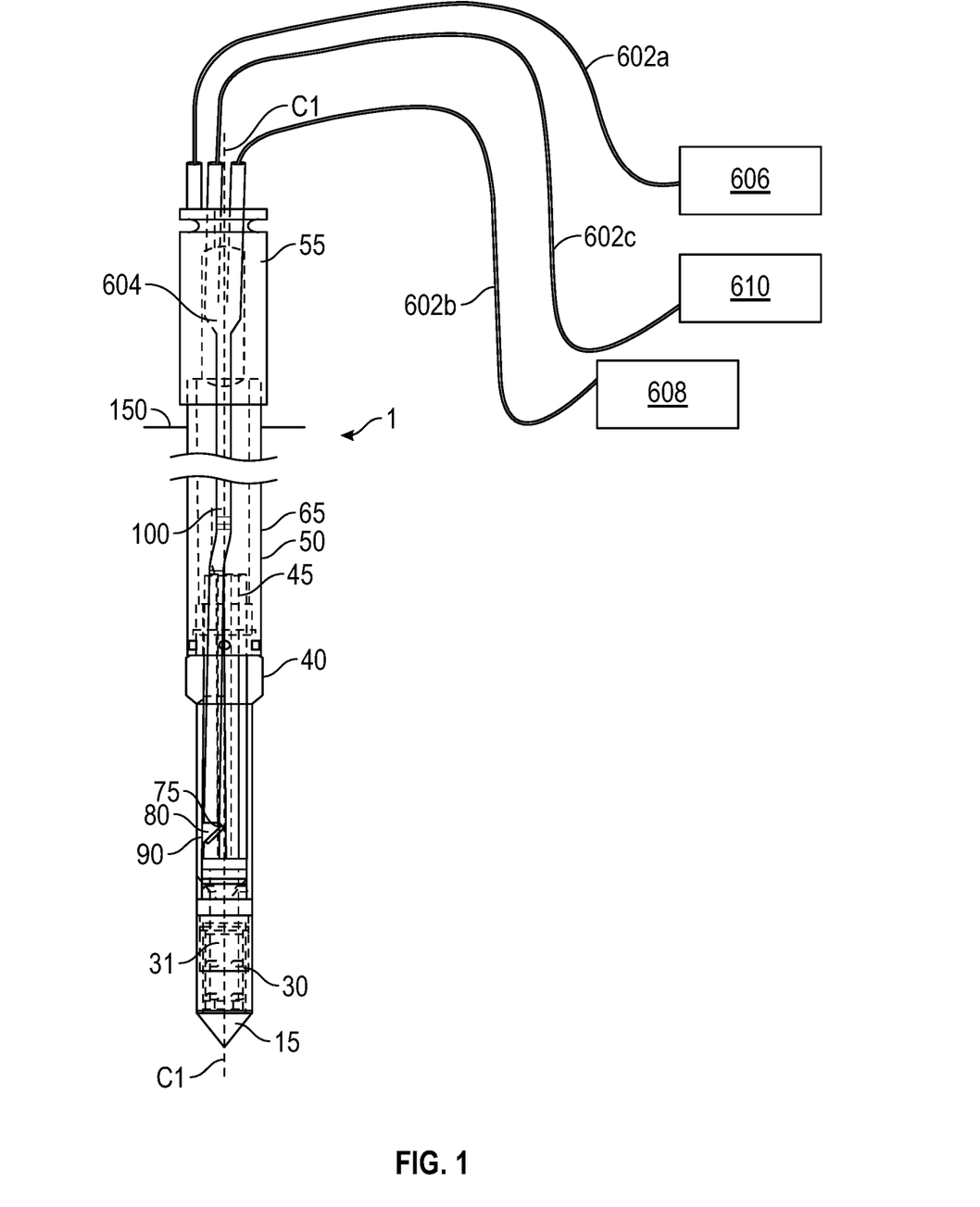
FIG. 1 is a side view of an embodiment of a spectral probe according to this disclosure.

FIG. 1 is a side view of one example implementation of an in-situ spectral probe 1, made in accordance with the present disclosure. Spectral probe 1 includes a fiber-optic bundle 100 for transmitting light for performing an in-situ spectral analysis of soil at a field location. Additionally, spectral probe 1 may include any of a variety of other sensors for concurrently collecting a plurality of measurements of the same region of a media 150, which can be used to characterize the media. By way of example, spectral probe 1 may also include a soil force sensor 30 incorporated into sleeve 31. Other examples of sensors include moisture sensors for collecting moisture measurements of the media and image sensors for collecting images of the media. spectral probe 1 is configured to be inserted into media 150, such as soil and other geologic elements, and perform spectrometry readings. The readings may be performed at various depths below a surface of the media 150 as the probe 1 is inserted into the media. In an example, soil force sensor 30 may be used to collect soil force data as the probe 1 is inserted into media 150 as well as other data, such as moisture and image data.

In the illustrated example, spectral probe 1 includes a housing 65 with a window 90, a mirror 80, a fiber-optic bundle 100, a light source 210 and a carriage 45. Fiber-optic bundle includes three legs 602a, 602b, and 602c, which are connected to a first spectrometer, which in the illustrated example, is a near infrared (NIR) spectrometer 606 configured to analyze electromagnetic radiation in the NIR spectral range. Probe 1 is also connected to a second spectrometer, which in the illustrated example is a visible (VIS) spectrometer 608 configured to analyze electromagnetic radiation in the VIS spectral range, and a light source 610, respectively. As described more below, in the illustrated example, light is transmitted from light source 610 down leg 602c and out of the probe through window 90 to illuminate a region of media 150 adjacent the window. The illumination source energy interacts with the sample under study to produce a signal that is coupled into the optical fibers in legs 602a and 602b which collect light, including light reflected by the media and transmit the collected light to spectrometers 606 and 608 for spectral analysis of the collected light which can be used to analyze and characterize the media. Unless otherwise specified the term light as used herein refers to electromagnetic radiation of any wavelength including electromagnetic radiation in the ultraviolet (UV), visible (VIS), or infrared, including near infrared (NIR), mid infrared (MIR), and far infrared (FIR).

In-situ spectral probes made in accordance with the present disclosure may be configured to perform any type of spectral analysis known in the art. By way of example, spectral probes of the present disclosure such as spectral probe 1 may be configured to perform diffuse reflectance spectroscopy (DRS), Raman spectroscopy, including resonance Raman spectroscopy, fluorescence spectroscopy, including single and multiphoton fluorescence spectroscopy, and light scattering analysis such as Mie scattering detection and analysis. The dimensions, chemical composition and make-up of the optical fibers in legs 602 are selected, designed, and configured according to the particular type of spectral analysis being performed and corresponding wavelengths of light that is transmitted.

In the illustrated example, housing 65 may include multiple in-line sections such as a probe tip 15, a sleeve 31, a sensor housing 40, a push rod 50, and a push rod adapter 55 (sometimes also referred to in the art as a push head). Sleeve 31, sensor housing 40, push rod 50, and push rod adapter 55 are tubular and formed about a central longitudinal axis C1.

In the illustrated embodiment, sensor housing 40 has a rectangular or square tubular cross section and the other sections 31, 50, and 55 have annular cross-sections. Tip 15 may be formed for ease of insertion into a media such as soil, wells, earth, etc., and may have various shapes and/or cross sections including conical, tapered, pointed, or triangular, and the tip 15 may also be formed about axis C1. Probe 1 may be configured for use with either a direct push machine or a rotary rig (not illustrated) for insertion into soil. For example, probe 1 may be coupled to a traveling ram of a direct push or rotary rig at push rod adapter 55 for raising and lowering the probe and for applying a downward force for driving the probe into the ground.

The sensor housing 40 is connected to the push rod 50 and the sleeve 31. One end of housing 65 is formed by the tip 15 which is connected to the sleeve 31. The other end of the housing is formed by the push rod adapter 55 which is connected to the push rod 50. Sections 15, 31, 40, 50, 55 may be integrally formed or separate sections that are connected through suitable methods such as adhesives, opposable threaded fasteners, rivets, screws, epoxies, etc. Additionally, sections 15, 31, 40, 50, 55 may be formed of the same or similar materials that are resistant to deformation upon insertion into media. For example, suitable materials may be three dimensionally stable materials including hard plastics, thermoplastics, metallic compounds or alloys (e.g., aluminum, stainless steel), ceramics, hard plastics, etc. The sections of probe 1 may be formed by a process corresponding to the chosen material such as metal milling, CNC machining, casting, ceramic molding, injection molding and additive manufacturing, etc. Tip 15 abuts and is connected to sleeve 31 by threaded fasteners or other methods as described above. Sleeve 31 may include a soil force sensor 30 and other types of sensors.

Figure 2:
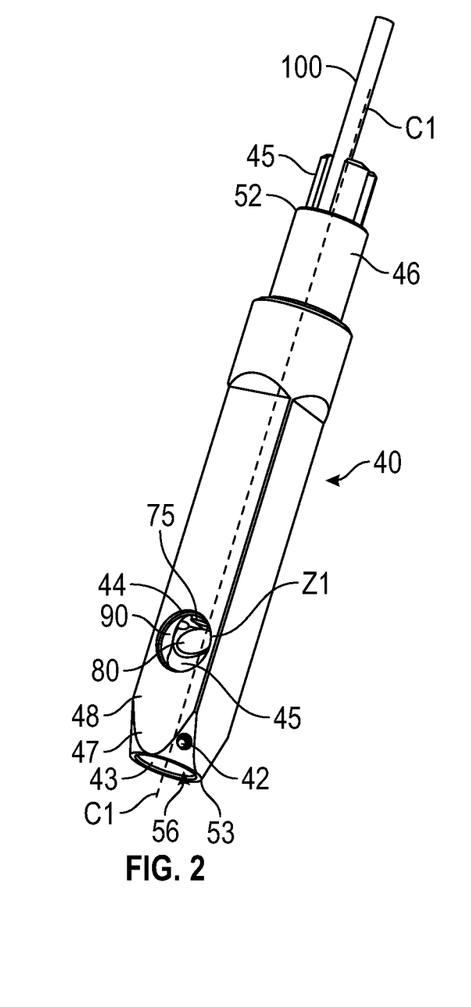
FIG. 2 is a front perspective view of a spectral sensor housing of the spectral probe of FIG. 1.
Figure 3:
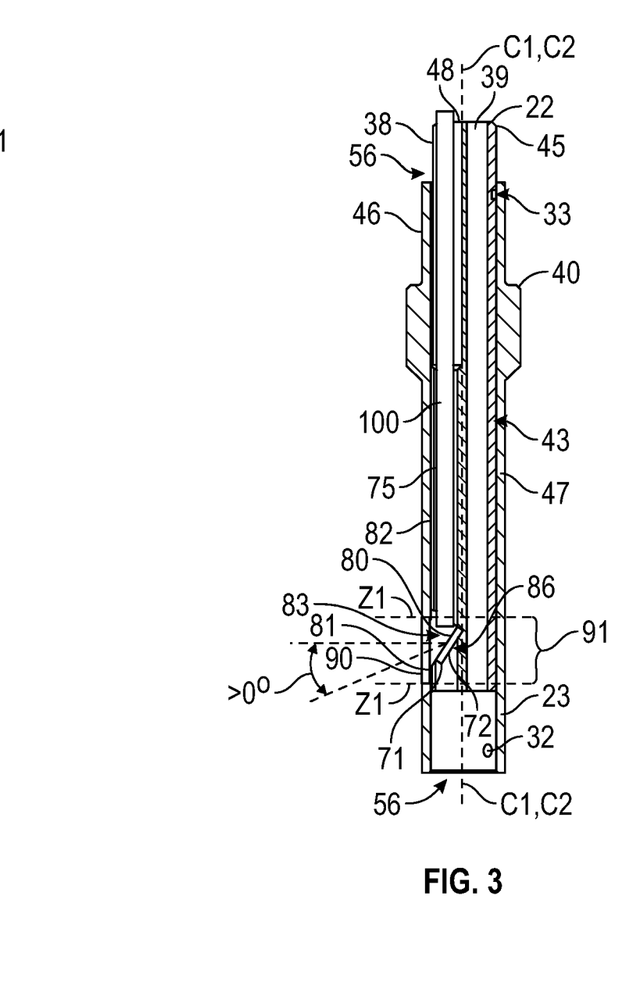
FIG. 3 is a longitudinal cross-sectional view of the spectral sensor housing of FIG. 2.

FIGS. 2-3 further illustrate example sensor housing 40. As shown, in the illustrated example, sensor housing 40 includes a tubular wall 48 having an exterior surface 47 and an interior surface 43 extending between a first end 52 and a second end 53. The interior surface 43 surrounds and defines a central opening 56 which also extends from the first end 52 to the second end 53. The first and second ends 52, 53 may be relatively smaller in diameter and/or width than a section of wall 48 therebetween. At the first end 52, sleeve section 46 is formed for insertion into push rod 50. Second end 53 tapers for connection with the sleeve 31. Through hole 42 positioned on the second end 53 allows connection to the sleeve 31 with a fastener 28 such as a pin, ribbed fastener or threaded fastener. Additionally, sleeve 46 and second end 53 may have features (not shown) such as threading and/or ridges for connection with the push rod 50 and sleeve 31.

An aperture 44 extends through the housing wall 48 and the exterior and interior surfaces 47, 43, respectively. A transparent material, such as a sapphire crystal or other material with suitable light transmissivity in the NIR spectral range, strength, and hardness, is disposed in and fills the aperture 44 and serves as a transparent window 90 in the wall 48 between a sampling end 75 of fiber-optic bundle 100 and external media 150. The window 90 may be secured in the aperture 44 by a marine adhesive or other suitable elements including epoxies, adhesives and/or a bracket, bezel, etc.

Carriage 45 may be disposed within sensor housing 40, as shown in FIG. 3. In an example, carriage 45 is secured to housing 40 by inserting a set screw into securing hole 33, in other examples other types of fasteners such as pins, threaded connections, or adhesives may be utilized. Carriage 45 is configured to hold a sensing-end portion of fiber-optic bundle 100, mirror 80 as well as other sensors and cables. To permit spectral measurements via window 90, carriage 45 is secured in position such that the sampling end 75 of fiber-optic bundle 100 and mirror 80 are adjacent and directly opposite the window. In the illustrated example, mirror 80 and sampling end 75 are within a zone 91 which is denoted by dashed line Z1 (see FIGS. 3 and 5). Line Z1 surrounds the perimeter of window 90 and extends within the boundaries of line Z1 surrounding the perimeter of the window surface 93 and into the housing 40 to the centerline C2 (see, e.g., FIG. 5). Zone 91 defines a three-dimensional zone in which sampling end 75 and mirror 80 may be placed so light 120 emitted from the sampling end may be reflected by the mirror 80 through the window 90 to media 150 and light can be efficiently collected by the sampling end. In the illustrated example, mirror 80 and sampling end 75 are laterally offset from a central longitudinal axis of the tubular housing and positioned directly laterally adjacent window 90.

In the illustrated example, window 90 is circular, but it is envisioned the window may be other shapes including square or rectangular. If the window 90 has different shapes then line Z1 would surround the perimeter of the window 90 and create a correspondingly shaped zone. In the illustrated example, zone 91 is a space envelope defined by an outer extent of window 90 that extends in a lateral direction across a width of the tubular housing and extends in an axial direction from a top edge of the window to a bottom edge of the window and the sampling end 75 and mirror 80 are located within the space envelope.

Figure 4:
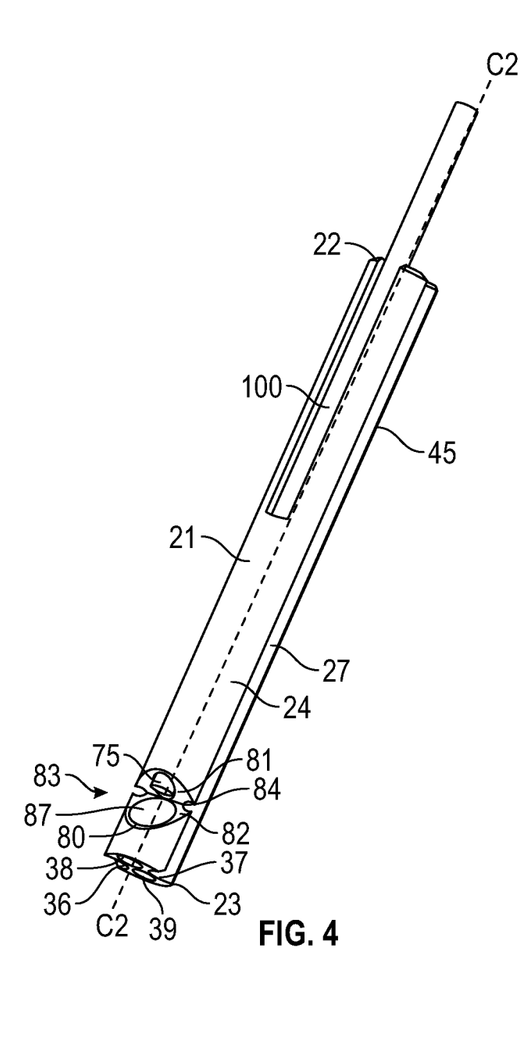
FIG. 4 is a perspective view of an embodiment of a carriage of the spectral probe of FIG. 1.

As shown in FIGS. 3 and 4, carriage 45 has a central longitudinal axis C2 which is coaxial and/or parallel to central longitudinal axis C1 of the housing 40 and a body 21 with an exterior surface 24 extending between a first end 22 and a second end 23. Carriage 45 may include a mirror recess 83, securing hole 33, sensor wire channels 36, 37 and sensor mounts 38, 39. The first end 22 is positioned within the first end 52 of housing 40 and the second end 23 may extend beyond the first end 52 of housing 40.

The carriage 45 may support several sensors. In the illustrated embodiment, the carriage includes sensor mounts 38 and 39 configured to hold sensors and/or sensing elements as well as wire channels 36 and 37 configured to hold sensor wiring. As shown, mount 39 is a through hole while channels 36 and 37, which also extend the length of the carriage 45, are defined by the exterior surface 24 with an opening 27 extending along the sides from the first end 22 to the second end 23 of the carriage 45. In this case, mount 38 holds fiber-optic bundle 100 and channel 37 may hold any other wiring (not shown) associated with other sensors such as the soil force sensor 30. It is envisioned that channels 36, 37 and mounts 38, 39 may each hold a sensor/sensing element and/or allow wires to pass through the carriage 45. Additionally, it is envisioned that more or fewer mounts, including varying dimensions, may be formed in carriage 45.

Figure 5:
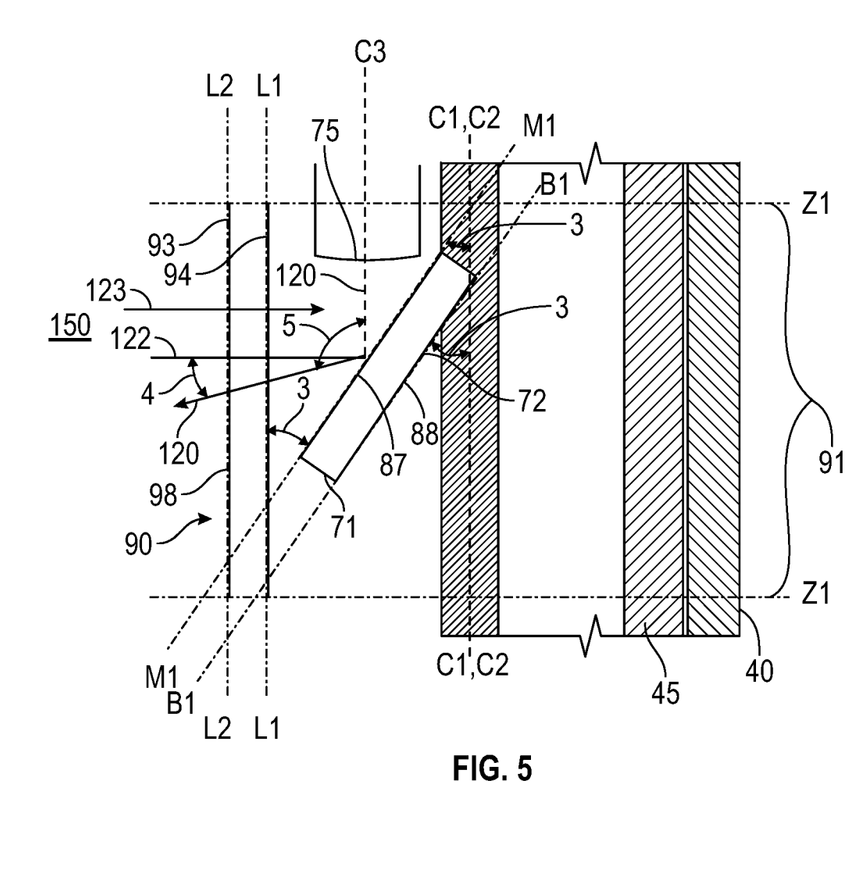
FIG. 5 is an enlarged cross-sectional view of a portion of the carriage of FIG. 4.

Mount 38 is a modified elongate longitudinal opening that extends along at least a portion of a length of the carriage 45. In the illustrated example a central axis of at least a portion of mount 38 is parallel to central axis C2. In other examples, at least a portion of mount 38 may be angled with respect to central axis C2 and not parallel to axis C2 for positioning at least a portion of fiber-optic bundle 100 at an acute angle with respect to axis C2. In the illustrated example mount 38 is a through hole as it appears open on the carriage first end 22 and second end 23. However, the mirror recess 83, as shown in FIGS. 3-5, is formed in the mount 38, carriage body 21, and exterior surface 24. Mirror recess 83 is a notched opening formed in exterior surface 24 of the carriage 45 that extends partially through a width of the carriage to, for example, centerline C2 of the carriage. The mirror recess 83 may be defined by a first surface 81 opposite and abutting a second surface 82 with the first and second surfaces 81, 82 extending outwardly and radially with respect to the centerline C2. At least first surface 81 intersects the sensor mount 38. An angle of surfaces 81 and 82 with respect to, e.g., centerline C2, may vary. In the illustrated example, surface 81 is at an acute angle with respect to centerline C2 which allows for sampling end 75 to protrude into mirror recess 83 and increases an interior volume partially defined by mirror recess 83 to increase an amount of reflected light from a soil sample that reaches the sampling end. In other examples, surface 81 may be at an angle that is about orthogonal to centerline C2. Additionally, the first surface 81 may extend axially towards the first end 22 and the second surface 82 may extend axially towards the second end 23. As shown, surfaces 81 and 82 may abut and may be contiguous at joint 84.

A mount recess 86 (FIG. 3) may be formed in the second surface 82. The mount recess 86 is configured to hold the mirror 80 with a bottom surface 72 and a sidewall 71. In an example, bottom surface 72 is substantially parallel to second surface 82 and sidewall 71 is at a right angle to bottom surface 72 and has a complementary shape to an outer perimeter of mirror 80 to locate the mirror in the mount recess 86. Like surface 82, bottom surface 72 extends radially and axially towards the second end 23. Additionally, the bottom surface 72 may extend entirely across the mount recess 86 or a portion of the mount recess 86. To ensure the mirror 80 is properly oriented towards the window 90, the bottom surface 72 is at an angle 3, as shown in FIG. 5 to a centerline C3 of sampling end 75 of fiber-optic bundle 100. Angle 3 extends between a plane B1 extending through and parallel to surface 72 and centerline C3. Due to the angle 3 of the bottom surface 72 on which the mirror 80 is mounted, a plane M1 extending through and parallel to mirror 80 is also positioned at the angle 3 to the centerline C3. In the illustrated example, angle 3 also extends between plane M1 and planes L1 and L2 extending across and parallel to window surfaces 94 and 93, respectively.

The mirror 80 has a reflective mirror surface 87 and mounting surface 88. In the illustrated example mirror 80 is flat, however, in other examples, other mirrors known in the art, such as a parabolic mirror, may be used. The mirror surface 87 faces both the sampling end 75 and window 90. Mounting surface 88 faces bottom surface 72 and away from the window 90. The mirror surface 87 and angle 3 are designed and configured for the mirror 80 to reflect light 120 emitted by sampling end 75 towards the window 90 for efficient transmission through the window to the media 150. The mirror 80 may be secured to surface 72 with a marine adhesive or other suitable elements including bonding agents (e.g., epoxies, adhesives) and/or fasteners. In the illustrated example, probe 1 does not include additional optical components, such as lenses, in the path between sampling end 75 and media 150. Such an arrangement allows for a compact design where sampling end 75 can be positioned closely adjacent to mirror 80 and both the sampling end and mirror can be positioned closely adjacent window 90, thereby shortening the optical path between the sampling end and the media and minimizing the space envelope that the window, mirror and sampling end encompass. The compact arrangement, with the optical components laterally offset from central longitudinal axes C1, C2 is also an efficient use of space within the probe that allows for incorporation of other sensing elements in the probe. In other examples, however, additional optical components, such as lenses and filters, may be incorporated into the optical path of the light 120.

In the illustrated example mirror 80 and reflective mirror surface 87 are suitable for reflection of light in at least the visible and NIR spectral ranges. One example of a suitable mirror is a protective gold mirror (e.g., sputtered or evaporated gold) coated with a thin protective dielectric film which may be a thin layer or multiple layers of a dielectric materials such as amorphous SiO2 or Si3N4 (silicon nitride). Such a mirror has a reflectivity of about >96% across the NIR spectral range, e.g., a spectral range of from about 780 nm to about 2500 nm.

FIG. 5 depicts an enlarged view of zone 91. As shown, mirror 80, sampling end 75 of fiber-optic bundle 100 and window 90 are disposed in zone 91. Due to the mirror angle 3, the mirror 80 may reflect light 120 emitted from the sampling end 75 towards window 90 at an angle 4 with respect to the window that is designed and configured for efficient transmission through the window to media 150. Media 150 reflects some portion of the light 121 as diffusely reflected light 123. Reflected light 123 is conceptually shown as a single arrow orthogonal to window 90, however, as will be appreciated by persons having ordinary skill in the art, the reflected light is diffuse and incident on the window across a range of angles. A portion of the reflected light 123 passes through the window 90 and is incident on sampling end 75 and then transmitted through one or more light receiver fibers e.g. fibers 612, 616 (FIGS. 7A-7D) to at least one spectrometer, e.g., spectrometers 606, 608, for spectral analysis.

Light 120 may be reflected from the mirror 80, through the window 90, to the media, with the angle of the mirror 80 being in a relatively large range. However, at some angles, a substantial proportion of light 120 incident on window 90 may be undesirably reflected by the first surface 94 and/or second surface 93 of the window rather than refracted and transmitted therethrough. These unwanted reflections may enter the sensor housing 40 and reach the sampling end 75 negatively impacting the ability of the probe to detect the signal of interest, i.e., light 123 reflected from the media 150 that passes through the window 90 to the sampling end 75. When this occurs, the light reflected by window 90 may cause the spectral analysis performed by probe 1 to be inaccurate. As a result, in some examples, probes made in accordance with the present disclosure may have a mirror 80 that is positioned at an angle 3 with respect to central longitudinal axis C3 of fiber-optic bundle 100 that is designed, configured, and selected to preclude or minimize the unwanted reflection of the light 120 by first and second surfaces 94, 93. By way of example, for some window materials, such as sapphire, if light 120 incident on window 90 is orthogonal to the window surface 94 (if angle 4 is 0°), a substantial proportion of the light will be reflected rather than transmitted. On the other hand for arrangements that result in light 120 having a relatively high value of angle 4, such an arrangement may also result in an insufficient proportion of the light 120 being transmitted through the window. In the illustrated embodiment, angle 3 is designed, configured and selected to minimize unwanted reflections from window 90 while maximizing a proportion of light transmitted through the window to increase a signal to noise ratio of the media spectral signal associated with reflected light 123.

Angle 3 illustrated in FIG. 5, defining an angle between mirror 80 and fiber-optic bundle 100, corresponds to the arrangement shown in FIG. 5 where the sampling end 75 of the fiber-optic bundle is positioned substantially parallel to window 90 with light 120 emitted by the sampling end similarly traveling in direction that is substantially parallel to the window. An angle between mirror 80 and window 90 is, therefore, the same as angle 3 in the illustrated example. In other examples, such as where sampling end 75 emits light 120 at another angle relative to window 90, angle 3 of mirror 80 relative to axis C3 may be the same while an angle of mirror 80 relative to window 90 may be correspondingly adjusted to an angle that is different from angle 3 to achieve the desired angle 4 of light 121 relative to window 90.

To preclude or minimize the proportion of light reflected by either the first or second surface 94, 93 from being incident on sampling end 75, a position of mirror 80 may be designed and configured so that the light 120 is incident on the first surface 94 of the window at an angle 4 in a range of about 14° to about 18°, and in some examples, about 16° from normal 122. With an angle of incidence 4, in the range of, e.g., about 14° to about 18°, the proportion of light reflected by window 90 may be substantially reduced or eliminated.

With an angle of incidence 4 in the range of about 14° to about 18°, the angle 5 between the light 120 emitted from the sampling end and the light 121 reflected by the mirror 80 is in an approximate range of about 104° to about 108°, and more specifically about 106°.

In the illustrated example, to achieve the angle of incidence 4 in the range of about 14° to about 18°, the mirror 80 is mounted at angle 3 with a range of about 35° to about 39° between the plane M1 and a central longitudinal axis C3 of sampling end 75. In the illustrated example, at least an end portion of the sensing element is positioned in a substantially parallel relationship to centerline C2 and so the angle between M1 and C3 is the same as the angle between the plane M1 of the mirror surface 87 and planes L1, L2 of window 90. To achieve the angle of incidence of about 16°, angle 3 may be about 37°. Therefore, mounting surface 72 within recess 86 may be formed such that it is at an angle 3 of about 35° to about 38° and in some examples about 37° from the centerline C3 of sampling end 75, and in some examples, also about 37° from the centerline C2 of the carriage 45. In other examples where sampling end 75 is not parallel to plane L1 of the first surface 94 of window 90, an angle of the mirror 80 relative to centerline C2 may be in a correspondingly different range so that the light 120 reflected by the mirror has the desired angle of incidence 4 with respect to the window. In an example, at least sampling end may be disposed at an angle within the carriage, for example, an angle between axes C2 and C3 may be in the range of about 1° to about 15°, and in some examples, in the range of about 2° to about 10°, and in some examples, about 5° and in some examples, about 2°. In such examples, an angular position of the mirror within the carriage may be adjusted so that the angle 3 between the mirror and the sensing element may be the same as in the illustrated example and an angle between the mirror surface 87 and the window (e.g. the angle between plane M1 and planes L1, L2) may be different. By way of non-limiting example, in an implementation where the angle between axes C2 and C3 is greater than zero and the sampling end 75 is pointing or tilted towards the window 9, an angle of the reflecting surface of the mirror relative to the first and/or second parallel surfaces of a transparent window may be greater than angle 3. In examples where the sampling end 75 is pointing or tilted away from the window 9, an angle of the reflecting surface of the mirror relative to the first and/or second parallel surfaces of a transparent window may be less than angle 3.

When light 123 is reflected from media 150, the light 123 may be transmitted into the sensor housing 40 through window 90 and reflected off of mirror 80 to the sampling end. The angle 3 of mirror 80, which in some examples may be in the range of about 35° to about 39°, may be designed and configured to also direct light 123 towards the sampling end 75. The foregoing angles are provided by way of example and may be varied according to a particular application. The foregoing angles may be suitable for a window material that is sapphire or another material with optical properties, such as index similar to sapphire and for efficiently reflecting a NIR portion of light 120 that has a wavelength in the range of about 750 nm to about 2500 nm or about 780 nm to about 2500 nm, or a portion thereof. The foregoing angles may also be suitable for light 120 that has a wavelength range that includes visible light, e.g. from about 380 nm to about 780 nm. Thus, in an example, an angle of the mirror is designed and configured to cause the near infrared light emitted by the sensing element to be reflected from the mirror and incident on a surface of the window at an acute angle with respect to an axis that is normal to the surface of the window, the acute angle designed and configured according to a wavelength of the near infrared light and a material type of the window to minimize a reflection of the near infrared light by the window while maximizing a transmission of the near infrared light through the window.

Figures 6, 7A, 7C:
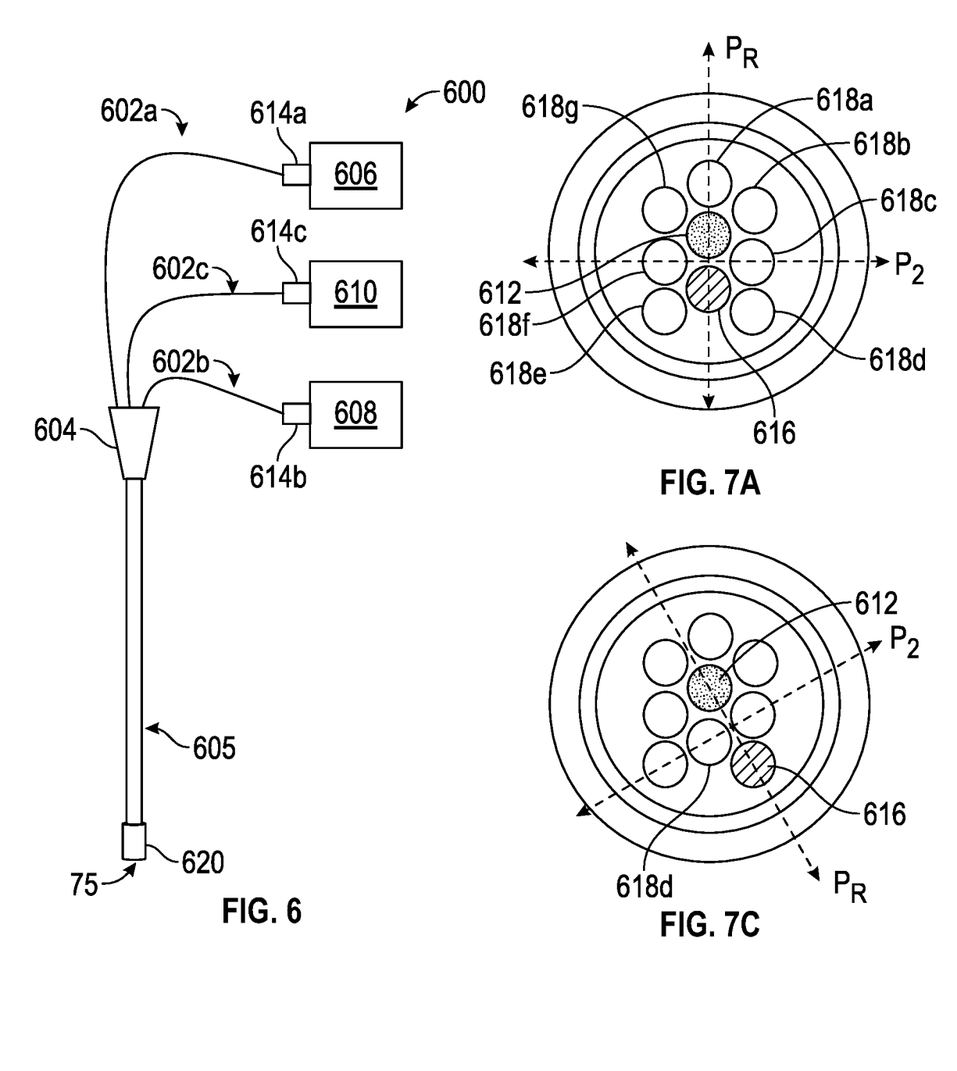
FIG. 6 is a schematic of an example implementation of a sensing system configured to be operably coupled to the spectral probe of FIG. 1, the sensing system including a fiber-optic bundle with an asymmetric spatial arrangement of illumination fibers.
FIGS. 7A-7D are end views of a sensing end of four example implementations of the fiber-optic bundle of FIG. 6.

FIG. 6 illustrates an example sensing system 600 that is designed to be operably coupled to a soil probe such as probe 1 for performing in-situ spectral analysis. Sensing system 60 includes fiber-optic bundle 100, which is an assembly that includes protective covers surrounding co-aligned arrangements of optical fibers capable of transmitting light in a spectral range that includes at least one of ultraviolet light (UV) in a range of about 200 nm to about 400 nm, visible (VIS) light in a range of about 380 nm to about 780 nm, NIR light in a range from about 780 nm to about 2500 nm, and/or MIR light in a range from about 2500 nm to about 16,500 nm. In the illustrated example, fiber-optic bundle 100 is a trifurcated fiber bundle including three legs 602a, 602b, and 602c, each of the legs including at least one optical fiber, that are joined at at least one fiber leg junction 604. The one or more optical fibers from each of the joined legs 602 extend along a common portion 605 to sampling end 75, which is configured to be disposed in a probe such as probe 1. Each of the legs 602 and the common portion 605 can be encased in any suitable protective covering, such as a steel fiber protective coil and in some cases a plastic outer sheath.

In the illustrated example sensing system 600 also includes IR spectrometer 606, VIS spectrometer 608, and light source 610. Leg 602a includes a first receiver fiber 612 (see FIG. 7A) and is connected to IR spectrometer 606 by a connector 614a. Leg 602b includes a second receiver fiber 616 and is connected to VIS spectrometer 608 by a connector 614b. And leg 602c includes a plurality of illumination fibers 618 and is connected to light source 610 by a connector 614c. In an example, one or more connectors 614a-614c may be a standardized commercial off the shelf connectors, such as a SMA905 connector, for ease of connection of the corresponding leg 602 to a commercial off the shelf spectrometer or light source.

The size, material type and numbers of fibers in legs 602a-602c may vary according to the type of spectral analysis probe 1 is designed to perform and the spectral ranges of light the fibers are designed to transmit. For example, in some examples, first and second receiver fibers 612, 616 in legs 602a and 602b may have different constructions and/or may be formed from different materials that are optimized for transmission of different wavelengths of light. For example, first receiver fiber 612 may be configured to transmit NIR light with a wavelength above about 750 nm or above about 900 nm or above about 1000 nm and second receiver fiber 616 may be configured to transmit visible light with a wavelength below about 1000 nm, or below about 900 nm, or below about 750 nm. First and second receiver fibers 612, 616 may be formed from any fiber optic materials now known or later developed and have a material and construction optimized for a particular wavelength range of light. In an example, one or both the first and second receiver fibers may have a core formed from fused silica (amorphous silicon dioxide, $SiO_2$) and/or a zirconia fiber, such as ZBLAN and/or may have a hollow core construction. In some examples, a concentration of hydroxyl groups (OH) in fibers 612 and 616 may be different, for example, first receiver fiber 612 may have a lower OH concentration to improve transmission in the NIR spectral range and second receiver fiber 616 may have a higher OH concentration or a mixture of higher and lower OH concentrations for better transmission at shorter wavelengths in the VIS spectral range. In other examples, either the first or second receiver fiber 612, 616 may have a core formed from other materials or may be doped with additional compounds to improve transmission over a particular spectral range. For example, for longer-wavelength applications, such as transmission of MIR light, one or more fibers in the fiber bundle may have a material or construction that is designed to efficiently transfer MIR light such as a chalcogenide glass, a germanate glass, a heavy metal fluoride glass, polycrystalline fiber made from, for example, a halide material, sapphire, a hollow waveguide, or other material now known in the art or later developed. Similarly, the fiber bundle may include fibers of other chemistries or constructions that are optimized for wavelengths longer than MIR or shorter than VIS-NIR.

In an example, first and second receiver fibers 612, 616 are multimode fibers and have a relatively large core diameter to increase the collection of light of interest, for example, a core diameter greater than about 300 μm, or greater than about 400 μm, or greater than about 500 μm, or about 600 μm. In some examples, a core diameter of first and second receiver fibers 612, 616 may be the same. In other examples, first receiver fiber 612 may have a larger core diameter than second receiver fiber 616 to maximize the collection of NIR photons and maximize a corresponding signal to noise ratio of the NIR measurement. First and second receiver fibers 612, 616 may have a cladding of any of a variety of thicknesses and material type, for example, they may have a glass cladding and the outer diameter of the cladding may be in the range of 50 μm to 200 μm greater than the core diameter.

IR spectrometer 606 may be any type of IR spectrometer known in the art or later developed. For example, IR spectrometer 606 may include an InGaAs or PbS based sensor, a Mercury-Cadmium-Telluride based sensor, or a VIS or near-VIS sensor and an upconverter for converting the IR light to VIS or near-VIS for detection and analysis, as is known in the art. Examples of commercially available spectrometers include an FT Rocket infrared spectrometer manufactured by ARCoptix located in Switzerland. A commercially available MIR spectrometer is a model number S2050 MIR spectrometer manufactured by NLIR located in Denmark. Similarly, VIS spectrometer 608 may be any type of VIS spectrometer known in the art or later developed. For example, VIS spectrometer 608 may include a CCD sensor for spectral analysis of visible light as is known in the art. In other examples, fiber-optic bundle 100 may include only two legs 602 and first and second receiver fibers 612 and 616 may be included in a single leg for connection to a single spectrometer capable of analyzing light in both IR and visible light ranges. For light source 610, any of a variety of light sources may be used, such as a light source that emits both visible, NIR, and in some cases MIR light, for example, a tungsten-halogen light source that emits light over a wavelength range from about 360 nm to about 2400 nm. In other examples two light sources may be used including an NIR or NIR-MIR light source to maximize illumination light in the NIR and/or MIR spectral ranges.

Illumination fibers 618 may similarly be formed from different materials and/or connected to light source(s) 610 having different spectral characteristics. In an example, illumination fibers 618 may also be multimode fibers with relatively large core diameters, such as core diameters in the range from 300 μm to 600 μm and the cores may be silica with low, high, or mixed OH concentration, or an alternate material or construction, including any of the example fiber material and construction types disclosed herein. Illumination fibers 618 may include a cladding of any material and thickness, such as a glass cladding with an outer diameter in the range of 50 μm to 200 μm greater than the core diameter.

As noted above, probe 1 may be coupled to a system, such as direct push machine or a rotary rig that raises and lowers the probe and in some cases pushes the probe into soil. Each of spectrometers 606 and 608 and light source 610 may be located on the direct push machine or rotary rig at a fixed location with legs 602 extending between the spectrometers or light source and the probe. In an example, fiber leg junction 604 may be affixed to probe 1, for example, located within push rod adapter 55 as shown in FIG. 1. Each of legs 602 may have a different and unique length for extending from probe 1 to a location on the larger system where a corresponding one of spectrometer 606, 608, or light source 610 is located. The glass material in the optical fibers of fiber-optic bundle 100 is relatively brittle and it is, therefore, desirable to minimize excessive movement and bending of the fibers. Thus, by providing separate legs 602, the lengths of the legs and corresponding fibers can be specifically tailored to a particular arrangement of a direct push or rotary system to provide an optimal length of each leg to minimize excessive movement and bending of the fibers in the legs 602 thereby improving durability and increasing the lifetime of the fiber-optic bundle 100.

Fiber-optic bundle 100 also includes a sampling head 620 that, as discussed more below, may be formed from a metal such as aluminum or steel that secures the ends of each of the fibers in an aligned orientation and in a desired geometric pattern to provide uniform illumination and maximize the signal to noise ratio of the VIS and NIR measurements.

As shown in FIGS. 3 and 6, fiber-optic bundle 100 including sampling end 75 and sampling head 620 is inserted into mount 38 of the carriage 45 and the fiber-optic bundle extends the length of the carriage. This length provides stability to the sampling end 75. Mount 38 holds sampling end 75 in a position which allows the illumination fibers 618 to emit light 120 in a desired direction, for example, substantially parallel to the first and second surfaces 94, 93 of the window 90 and corresponding planes L1, L2 as well as central longitudinal axes C1, C2. In other examples, light 120 emitted by sampling end 75 may be at an acute angle relative to window 90. Fiber-optic bundle 100 may abut an interior surface 49 of the mount 38 and be held in place by various methods including a friction fit, epoxy, adhesives, fasteners, etc.

FIGS. 7A-7D are end views of sampling end 75 of fiber-optic bundle 100 illustrating four alternative examples of spatial arrangements of the optical fibers in the fiber-optic bundle. Referring to FIG. 7A, in the illustrated example, fiber-optic bundle 100 includes seven illumination fibers 618a-618g connected to light source 610, first receiver fiber 612 connected to IR spectrometer 606 and second receiver fiber 616 connected to VIS spectrometer 608. In the example shown in FIG. 7A each fiber in bundle 100 has approximately the same core size and in an example each may be a large-core multimode fiber having a core diameter in the range of, e.g., about 400 μm to about 600 μm.

In the example shown in FIG. 7A, the plurality of illumination fibers 618 are arranged in an asymmetric pattern that is designed and configured to generate a first illumination intensity incident on the first receiver fiber 612 and a second illumination intensity incident on the second receiver fiber 616, wherein the first illumination intensity is greater than the second illumination intensity. A signal to noise ratio (SNR) for IR measurements, such as NIR measurements, such as those performed by an in-situ sampling probe like probe 1 can be relatively low as compared to a VIS measurement. The SNR of the NIR or MIR measurement can be increased by increasing a uniformity and/or intensity of illumination light used for the IR measurement. In the illustrated example, the asymmetric spatial pattern of the illumination fibers 618 results in a greater proportion of the total illumination intensity emitted by the illumination fibers being incident on first receiver fiber 612, thereby improving the IR measurement.

Fiber-optic bundle 100 is designed and configured to increase the SNR of the IR measurement by increasing a light intensity incident on the IR receiver fiber (first receiver fiber 612) by the spatial arrangement of the illumination fibers 618 relative to the first receiver fiber at sampling end 75. In the illustrated example, the light intensity incident on first receiver fiber 612 is an intensity of diffusely reflected light that has travelled the optical paths associated with the illustrated arrangement, including window 90, mirror 80, and media 150. As compared to an NIR spectrometer, the SNR of a visible light measurement performed by a VIS spectrometer such as VIS spectrometer 608 is generally higher and less light intensity is needed to obtain an adequate measurement. Also, for many light sources the relative energy of the spectral radiation output of the light source is greater in the VIS wavelength range than the NIR wavelength range such that directing a greater proportion of the total illumination to the NIR receiver fiber 612 than the VIS receiver fiber 616 provides a more equalized and improved overall measurement result. Illumination fibers 618 are, therefore, arranged in a pattern that directs a greater proportion of the total light emitted by the illumination fibers 618 to the first receiver fiber 612 and a smaller proportion of the total light is directed to the second receiver fiber 616. In the illustrated example of FIG. 7A this is achieved by positioning an additional illumination fiber, 618a, directly adjacent first receiver fiber 612, resulting in an asymmetric arrangement that directs a greater amount of light, here light that was diffusely reflected by media 150, in the vicinity of the first receiver fiber than the second receiver fiber 616. By omitting an additional illumination fiber from the corresponding space on the opposite side of the bundle adjacent second receiver fiber 616, valuable space can be saved. The core diameters of illumination fibers 618 and receiver fibers 612 and 616 can be maximized while working within external constraints, such as a size of connectors 614.

In the arrangement shown in FIG. 7A, the asymmetrical arrangement of illumination fibers 618 includes a bilaterally symmetric arrangement of four of the illumination fibers (618c, 618d, 618e, and 618f) directly and tangentially adjacent second receiver fiber 616. The illumination pattern for the NIR fiber (first receiver fiber 612) approximates a round, 6-around-1, pattern by deriving a combined effect from two illumination fibers, 618d, 618e, spaced from the first receiver fiber by a distance approximately equal to a diameter of the second receiver fiber 616. Illumination fibers 618d, 618e approximate a position of a phantom sixth illumination fiber in the 6-around-1 pattern in the location occupied by the visible receiver fiber (second receiver fiber 616). A first group of illumination fibers 618 (illumination fibers 618a, 618b, 618c, 618f, and 618g) and second receiver fiber 616 are, therefore, positioned in a circular pattern within an annular space envelope and first receiver fiber 612 is positioned in the middle of the circular pattern. A second group of illumination fibers 618 (fibers 618d and 618e) are directly adjacent the second receiver fiber 616.

In the arrangement shown in FIG. 7A, the centers of the sampling ends of the first and second receiver fibers 612, 616 are positioned in a receiver fiber plane, $P_R$, that is parallel to a central longitudinal axis of sampling head 620 and the receiver fibers are positioned on opposite sides of a second plane, $P_2$, that is perpendicular to the receiver fiber plane $P_R$. A total surface area of the sampling ends of the illumination fibers 618 is greater on the first-receiver-fiber-side of the second plane $P_2$ than the opposite, second-receiver-side, of the second plane $P_2$.

Figure 7B:
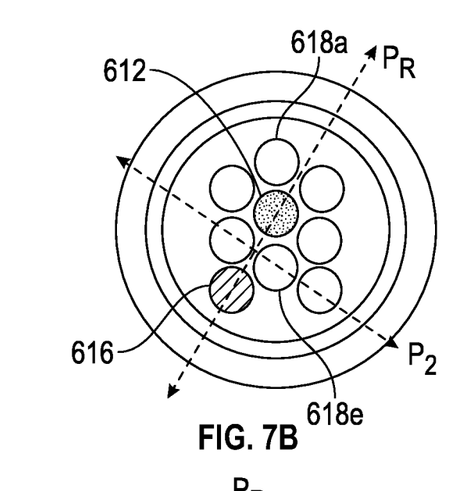

FIGS. 7B and 7C illustrate alternate examples of sampling end 75 of fiber-optic bundle 100 with alternate spatial arrangements that result in a greater illumination intensity at the first receiver fiber 612 than the second receiver fiber 616. Comparing the arrangements shown in FIGS. 7B and 7C to FIG. 7A, the position of the second receiver fiber 616 has been moved radially outward and exchanged with illumination fiber 618e or 618d.

Figure 7D:
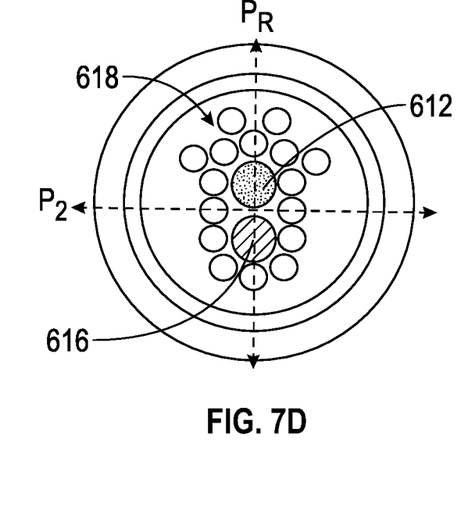

FIG. 7D shows another example arrangement of fibers in fiber-optic bundle 100. In the example shown in FIG. 7D, a diameter of the illumination fibers 618 is less than the diameter of receiver fibers 612, 616 and a number of the illumination fibers has been increased. As with the examples shown in FIGS. 7A-7C, FIG. 7D illustrates an asymmetrical arrangement of the illumination fibers 618 resulting in a greater illumination intensity at the first receiver fiber 612 than the second receiver fiber 616.

As with the example shown in FIG. 7A, in each of the examples shown in FIGS. 7B-7D the plurality of illumination fibers 618 are arranged in an asymmetric pattern that is designed and configured to generate a first illumination intensity incident on the first receiver fiber 612 and a second illumination intensity incident on the second receiver fiber 616, wherein the first illumination intensity is greater than the second illumination intensity. Also as with the arrangement shown in FIG. 7A, in each of the arrangements in FIGS. 7B-7D, the centers of the sampling ends of the first and second receiver fibers 612, 616 are positioned in a receiver fiber plane $P_R$ that is parallel to a central longitudinal axis of sampling head 620 and the receiver fibers are positioned on opposite sides of a second plane $P_2$ that is perpendicular to the receiver fiber plane $P_R$. A total surface area of the sampling ends of the illumination fibers 618 is greater on the first-receiver-fiber-side of the second plane $P_2$ than the opposite, second-receiver-side, of the second plane $P_2$.

Figure 8A:
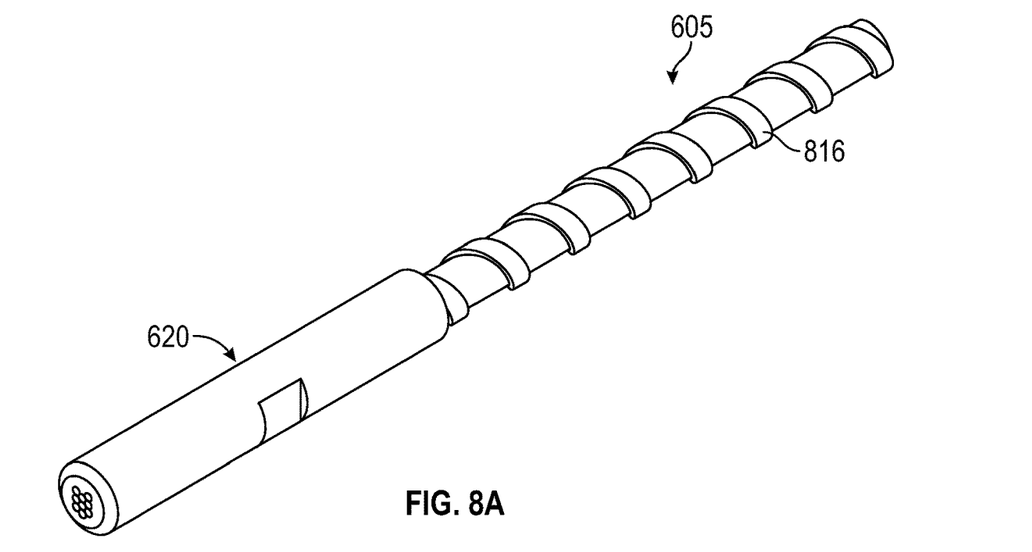
FIG. 8A is a perspective view of an example of a sampling head of the fiber-optic bundle of FIG. 6.
Figure 8B:
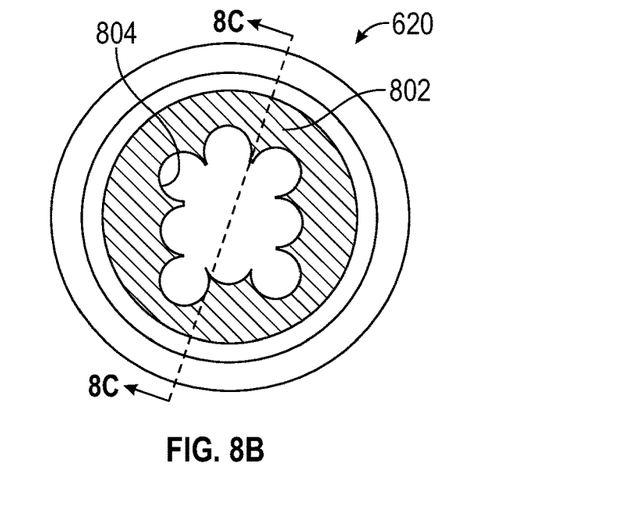
FIG. 8B is an end view of the sampling head of FIG. 8A.
Figure 8C:
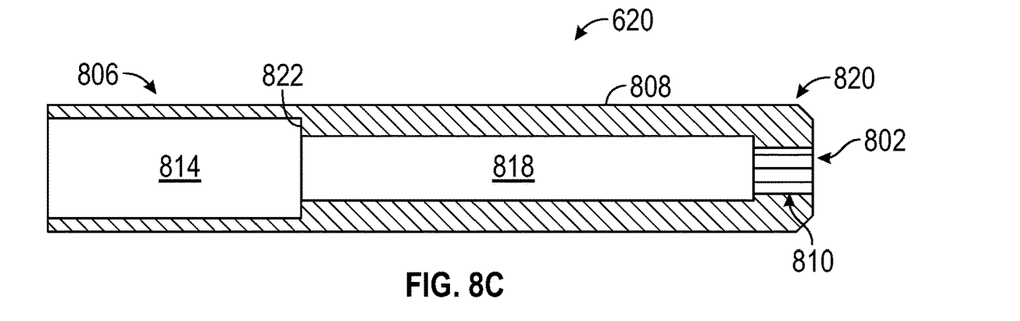
FIG. 8C is a cross sectional view of the sampling head of FIGS. 8A and 8B.

FIGS. 8A-8C illustrate sampling head 620 with the optical fibers removed. In the illustrated example, sampling head 620 includes a fixture 802 that is designed and configured to receive and hold the sampling ends of each of the plurality of optical fibers in fiber-optic bundle 100 in a desired spatial arrangement to ensure a specific spatial arrangement and pattern of the plurality of fibers is maintained during assembly and manufacture of the fiber-optic bundle. In the illustrated example fixture 802 is a solid piece, such as a solid piece of metal, that has been machined with a contoured inner wall 804 (see FIG. 8B) that has a shape that is complementary to a shape of an outer extent of the arrangement of the plurality of optical fibers. In the illustrated example a shape of inner wall 804 includes a plurality of elongate sections 810 positioned around a circumference of the inner wall, each of the plurality of sections having an arcuate cross sectional shape with a radius that is approximately the same as an outer radius of a corresponding optical fiber that will be positioned in a given arcuate section. In the example shown in FIGS. 8A-8C, inner wall 804 has been machined to provide a fixture for manufacturing any of the patterns shown in FIGS. 7A-7C. As best seen in FIG. 8C, which is a longitudinal cross sectional view of sampling head 620, in the illustrated example, the sampling head is a unitary cylindrical member that includes a wall 806 having an outer surface 808, a first portion 814 having a first inner diameter, a second portion 818 having a second inner diameter that is smaller than the first inner diameter, thereby forming a shelf 822. Sampling head 620 also includes a fixture portion 820 that includes fixture 802. An end of an outer sheath 816 (see FIG. 8A) is disposed in first portion 814 and abuts shelf 822 and the optical fibers in bundle 100 extend beyond the end of the sheath to fixture portion 820.

Figure 9:
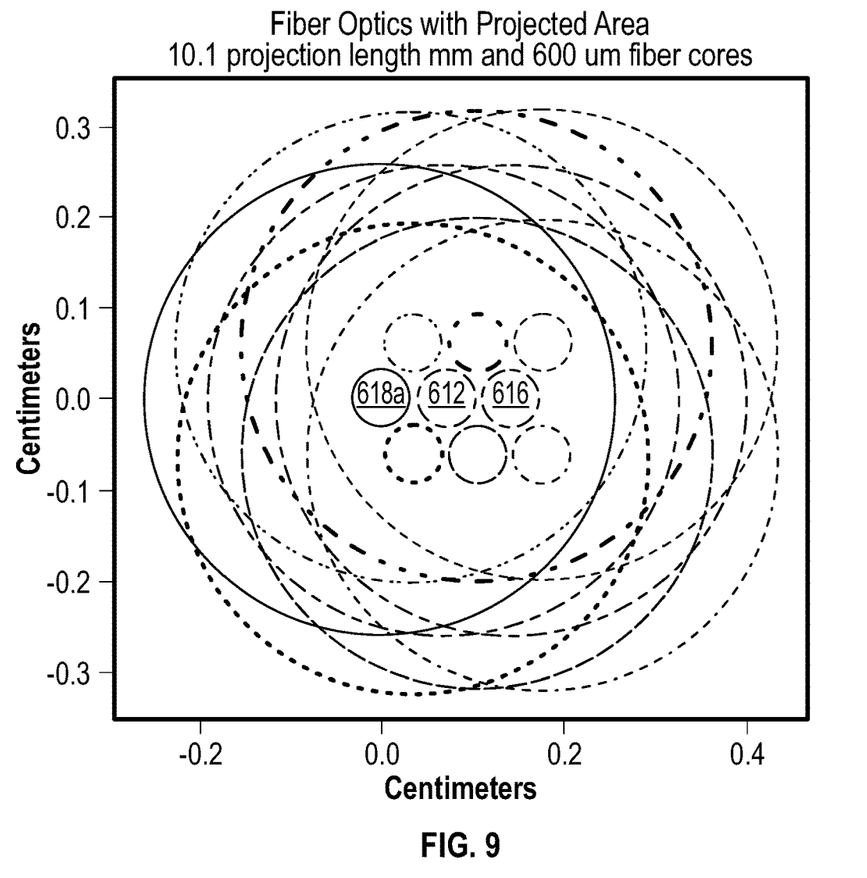
FIG. 9 illustrates an illumination pattern for the optical-fiber bundle arrangement illustrated in FIG. 7A.

FIG. 9 illustrates an illumination pattern for the optical-fiber bundle arrangement illustrated in FIG. 7A incident on a target that is 10.1 mm from sampling end 75 and parallel to the sampling end and normal to central longitudinal axis of the illumination fibers 618. FIG. 9 also illustrates the intersection of the acceptance cones of the first and second receiver fibers 612, 616 and the target, which are a function of the numerical aperture of the receiver fibers and the distance between the ends of the fibers and the target. In the example shown in FIG. 9 each of the fibers has the same numerical aperture, which is 0.22 in the illustrated example. FIG. 9 illustrates the asymmetrical illumination pattern that results from the arrangement shown in FIG. 7A, which increase an intensity of light received by first receiver fiber 612 thereby improving the NIR measurement.

Figure 10:
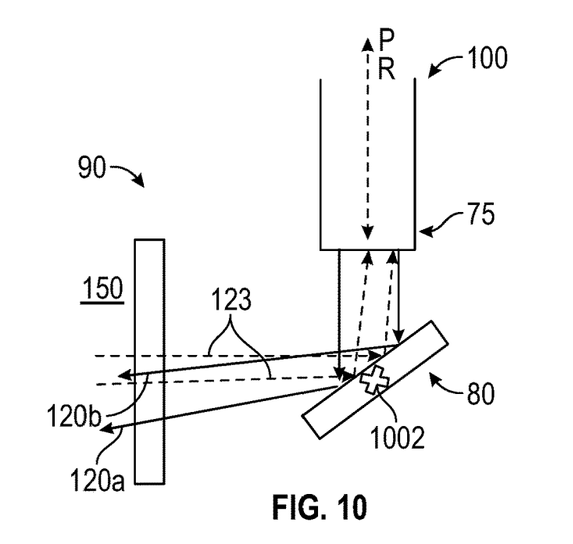
FIG. 10 is a schematic diagram illustrating a spatial arrangement of certain optical components of the spectral probe of FIG. 1.

FIG. 10 illustrates fiber-optic bundle 100 mirror 80 and window 90 of probe 1. As described above, in an example, fiber-optic bundle 100 is designed and configured to be positioned in probe 1 with sampling end 75 adjacent mirror 80 and window 90. Illumination fibers 618 emit light 120 which reflects off mirror 80 and transmits through window 90 and illuminates media 150, e.g., soil. A portion of light 120 is reflected by media 150 as reflected light 123, some of which enters the acceptance cones of the first and second receiver fibers 612, 616 either by direct transmission from window 90 to sampling end 75 or via reflection off of mirror 80.

In examples that include two receiver fibers 612, 616 and an angled mirror such as mirror 80, a distance between the receiver fibers to the mirror and, in some cases, the projection length from each of the receiver fibers to the media 150 can vary as a function of a relative rotational position of sampling end 75 with respect to the mirror. As noted above in connection with FIGS. 7A-7D, the receiver fibers 612, 616 can be positioned along a receiver fiber plane $P_R$.

In an embodiment, a rotational position of receiver fiber plane $P_R$ relative to a central transverse axis 1002 of mirror 80 about which the mirror is angled can be designed configured and selected to achieve a desired result, such as maximize a SNR of NIR and/or MIR measurements obtained by IR spectrometer 606. In one example, fiber-optic bundle 100 is positioned so that receiver fiber plane $P_R$ is parallel to mirror axis 1002 (an angle of 0° between receiver fiber plane $P_R$ and mirror axis 1002) resulting in a distance from the ends of receiver fibers 612, 616 to mirror 80 being the same.

In another example, fiber-optic bundle 100 is positioned so that receiver fiber plane $P_R$ is perpendicular to mirror axis 1002 (an angle of +90° between receiver fiber plane $P_R$ and mirror axis 1002) and with first receiver fiber 612 (e.g., the NIR receiver fiber) being positioned closer to mirror than second receiver fiber 616, also resulting in a horizontal distance from window 90 to the first receiver fiber being greater than a horizontal distance between the window and the second receiver fiber.

In another example, fiber-optic bundle 100 is positioned so that receiver fiber plane $P_R$ is perpendicular to mirror axis 1002 and with first receiver fiber 612 (e.g., the NIR receiver fiber) being positioned farther from the mirror than second receiver fiber 616 (an angle of −90° between receiver fiber plane $P_R$ and mirror axis 1002), also resulting in a horizontal distance from window 90 to the first receiver fiber being less than a horizontal distance between the window and the second receiver fiber.

In yet other examples an angle between receiver fiber plane $P_R$ and mirror axis 1002 may be any value in a range between about −90° and +90°, and in some examples between about −45° and +45°, or between about −90° and 0°, or between about 0° and +90°, or between about −45° and 0°, or between about 0° and +45°, or between about −45° and −10°, or between about 10° and +45°.

Figures 11A, 11B, 11C:
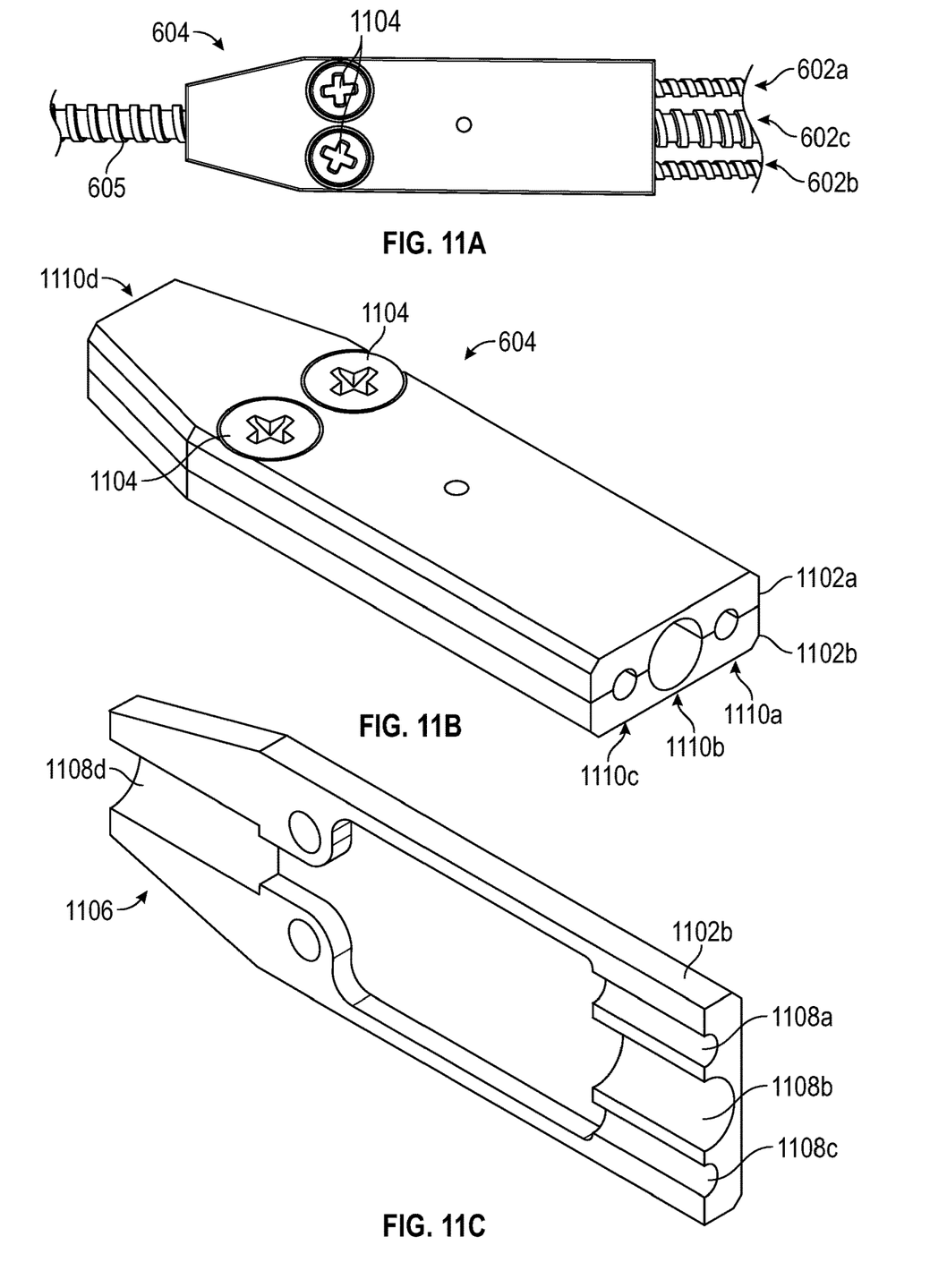
FIGS. 11A-11C illustrate a fiber leg junction of the fiber-optic bundle of FIG. 6.

FIGS. 11A-11C illustrate one example implementation of fiber leg junction 604 made in accordance with the present disclosure. In the illustrated example fiber leg junction 604 is made up of first and second portions 1102a, 1102b that are secured together by fasteners 1104, e.g., screws or bolts. Both portions 1102a and 1102b are unitary metal portions. FIG. 11C illustrates an interior side 1106 of second portion 1102b and shows recesses 1108a, 1108b, 1108c, and 1108d formed in the second portion. First portion 1102a similarly includes recesses that together with recesses 1108a-d form channels 1110a-1110d that are sized to receive corresponding fiber legs 602 and common portion 605.

Figure 12:
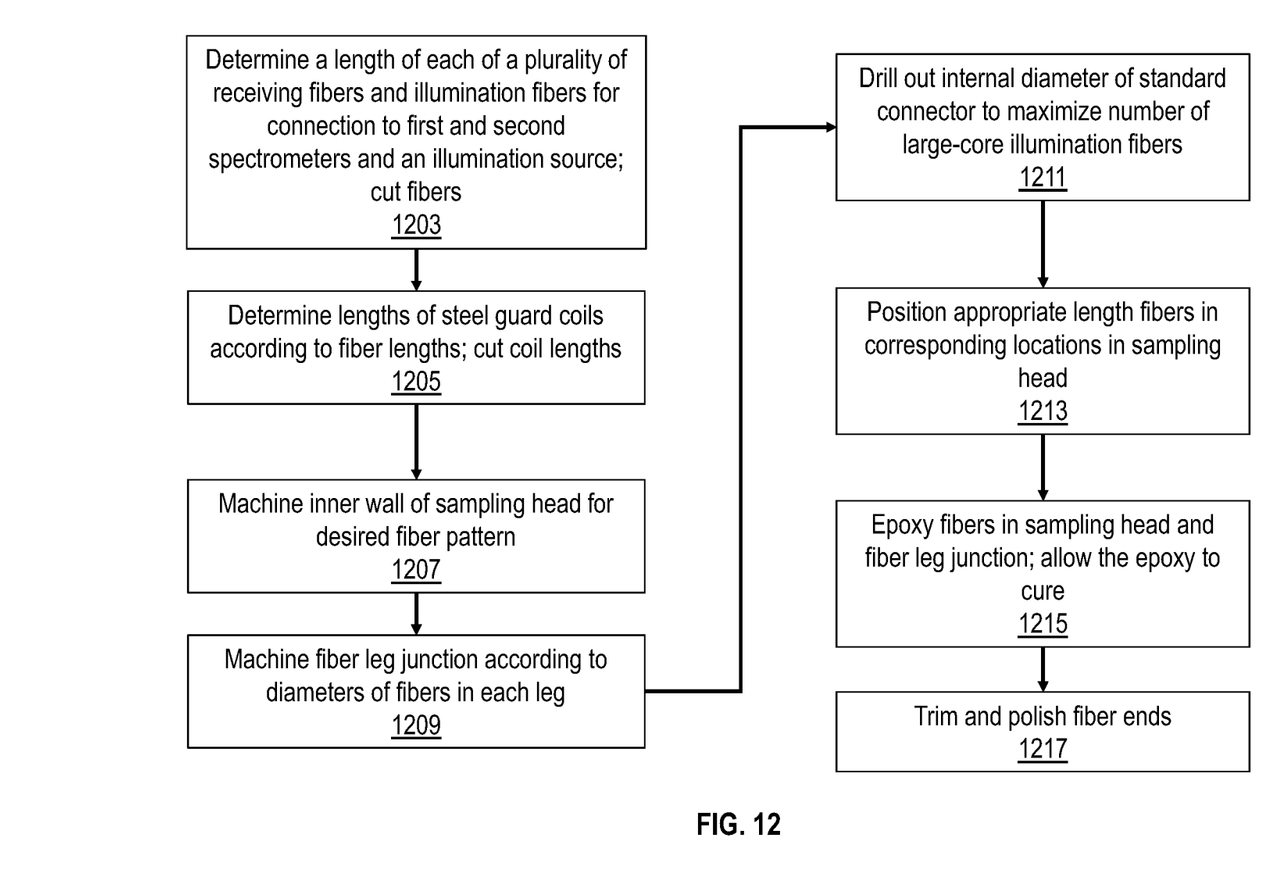
FIG. 12 is a flow chart illustrating an example method of manufacturing a fiber-optic bundle.

FIG. 12 illustrates an example method 1200 for manufacturing a fiber-optic bundle, such as fiber-optic bundle 100 for use with a ground-penetrating probe, such as probe 1, for performing spectral analysis of a media, such as soil. In the illustrated example, method 1200 includes, at block 1203, determining a length of each of a plurality of receiver fibers, such as first receiver fiber 612 and second receiver fiber 616, and a length of a plurality of illumination fibers, such as illumination fibers 618, for connection to first and second spectrometers, such as IR spectrometer 606 and VIS spectrometer 608, and an illumination source, such as light source 610 and then cutting the fibers at the determined lengths. It can be a distinct advantage to specifically tailor the lengths of the fibers for a particular system the fiber-optic bundle is designed to be used with to minimize stress, strain and bending as much as possible during use of the fiber-optic bundle. Thus, the steps at block 1203 can include determining a length from a ground penetrating probe to a location where spectrometers and light sources are located, such as where they are attached to a ground-penetrating push rig system and preparing fibers of different lengths for connecting to specific locations in the system. At block 1205, method 1200 may include determining lengths of steel guard coils according to the previously-determined fiber lengths and cutting the coil lengths.

At block 1207, method 1200 may include machining an inner wall of a sampling head, such as sampling head 620, according to a desired fiber pattern. As noted above, the sampling head can be machined to a shape that is designed and configured as a fixture for holding specific fibers in specific locations, which can be advantageous for facilitating manufacturing a fiber bundle with a specific spatial pattern of fibers for a desired illumination pattern and intensity with respect to the plurality of receiver fibers.

At block 1209, method 1200 may include machining a fiber leg junction according to the diameters of the fibers in each leg. In an example, block 1207 may include forming a plurality of unitary metal portions, such as portions 1102a, 1102b (FIGS. 11A, 11B) at least some of the unitary portions including channels for positioning one or more optical fibers.

At block 1211, method 1200 may include drilling out an internal diameter of a standard connector, such as a SMA905 connector, to maximize a number of large-core illumination fibers, such as illumination fibers 618, that can extend through the connector while maintaining a sufficient minimum wall thickness of the connector. As noted above, it can be advantageous to use a standard connector, such as a SMA905 connector, for connecting the legs of the fiber-optic bundle (e.g., legs 602) to other devices so that commercial off the shelf devices can be readily used. It can also be advantageous to maximize an illumination intensity of light transmitted by the illumination fibers, which can be increased by increasing a total cross sectional surface area of the illumination fibers. In the illustrated example, seven large-core-diameter illumination fibers 618 are utilized and to maximize the allowable diameter of each fiber, at block 1211, the connector, such as connector 614c (FIG. 6), may be a modified version of a standard commercial off the shelf connector. In an example, block 1211 may include the steps of obtaining a standard commercial off the shelf connector, such as a SMA 905 connector, which has an inner wall that defines a first inner diameter, and machining the inner wall to increase the inner diameter to be large enough to receive the plurality of illumination fibers 618. The machining step also results in a thickness of a wall of the connector being reduced. In an example, block 1211 may also include the step of adding a reinforcing layer to an outer side of the commercial off the shelf connector to increase the strength and durability of the connector despite the reduced wall thickness.

At block 1213, method 1200 may include positioning the appropriate-length fibers in corresponding locations in the sampling head according to a desired fiber pattern. As noted above, the specially-shaped sampling head formed at block 1207 can make assembly of the fibers, which are relatively thin and delicate, in a particular spatial pattern, much easier by holding the fibers in the desired location in the sampling head.

At block 1215, method 1200 may include epoxying the fibers in the sampling head and the fiber leg junction and allowing the epoxy to cure. And at block 1217, trimming and polishing the fiber ends.

Aspects of the present disclosure include a method of manufacturing a fiber-optic bundle, the method comprising:
obtaining a plurality of optical fibers that include a first receiver fiber, a second receiver fiber, and a plurality of illumination fibers; and
arranging the plurality of illumination fibers in an asymmetric pattern at a sampling end of the fiber-optic bundle, wherein the asymmetric pattern is designed and configured to provide a first illumination intensity incident on the first receiver and a second illumination intensity incident on the second receiver fiber, wherein the first illumination intensity is greater than the second illumination intensity.

Aspects of the present disclosure include the method of the paragraph immediately above, further comprising:
obtaining a sampling head that includes a central fixture having a contoured inner wall having a shape that is complementary to a shape of an outer extent of the plurality of optical fibers; and
selectively positioning a sampling end of each of the plurality of optical fibers in the central fixture to form the asymmetric pattern, wherein the contoured wall maintains the sampling ends of the optical fibers in a fixed orientation to facilitate maintaining the asymmetric pattern during assembly of the fiber-optic bundle.

Aspects of the present disclosure include the method of one or the other of the two paragraphs immediately above, further comprising:
arranging the plurality of optical fibers into three legs, a first one of the legs including a plurality of illumination fibers;
obtaining a commercial off the shelf connector for connecting the first one of the legs to a light source; and
machining an internal diameter of the connector to increase a size of the internal diameter to maximize a total cross sectional area of core diameters of the plurality of illumination fibers disposed in the first leg.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as generally defined in the appended claims.

The foregoing has been a detailed description of illustrative embodiments of the disclosure. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this disclosure. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present disclosure. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this disclosure.

What is claimed is:

1. A fiber-optic bundle, comprising:
a sampling end; and
a plurality of optical fibers that include:
a first receiver fiber;
a second receiver fiber; and
a plurality of illumination fibers arranged in an asymmetric pattern at the sampling end, wherein the asymmetric pattern is designed and configured to provide a first illumination intensity incident on the first receiver fiber and a second illumination intensity incident on the second receiver fiber, wherein the first illumination intensity is greater than the second illumination intensity.

2. The fiber-optic bundle of claim 1, wherein the asymmetric pattern includes a circular arrangement of a first group of the illumination fibers and the second receiver fiber and the first receiver fiber located in the middle of the circular arrangement.

3. The fiber-optic bundle of claim 2, wherein the asymmetric pattern further includes a second group of the illumination fibers positioned outside of the circular arrangement and directly adjacent the second receiver fiber.

4. The fiber-optic bundle of claim 3, wherein a number of the illumination fibers in the first group of illumination fibers is greater than a number of the illumination fibers in the second group of illumination fibers.

5. The fiber-optic bundle of claim 1, wherein the asymmetric pattern includes a round pattern that includes a first group of the illumination fibers and the second receiver fiber positioned in an annular space envelope and the first receiver fiber located in the middle of the annular space envelope, wherein the illumination fibers include a second group of fibers located at least partially radially outside of the annular space envelope.

6. The fiber-optic bundle of claim 1:
wherein a sampling end of the first receiver fiber and a sampling end of the second receiver fiber are positioned in a receiver fiber plane;
wherein the sampling end of the first receiver fiber is located on a first side of a second plane and the sampling end of the second receiver fiber is located on a second side of the second plane, wherein the second plane is perpendicular to the receiver fiber plane;
wherein each of the plurality of illumination fibers includes a sampling end, wherein a total surface area of the sampling ends of the plurality of illumination fibers located on the first side of the second plane is greater than a total surface area of the sampling ends of the plurality of illumination fibers located on the second side of the second plane.

7. The fiber-optic bundle of claim 1, wherein the first receiver fiber is configured to be connected to an infrared spectrometer and configured to transmit at least one of near-infrared or mid-infrared light and the second receiver fiber is configured to be connected to a visible light spectrometer and configured to transmit visible light.

8. The fiber-optic bundle of claim 7, wherein the first receiver fiber has at least one of a different chemical composition, different core diameter, or different construction than the second receiver fiber.

9. The fiber-optic bundle of claim 7, wherein a core material of the first receiver fiber has a lower concentration of hydroxyl groups than a core material of the second receiver fiber.

10. The fiber-optic bundle of claim 1, wherein the first illumination intensity and the second illumination intensity are each an intensity of diffusely reflected light reflected by media.

11. The fiber-optic bundle of claim 10, wherein the diffusely reflected light travels along an optical path in an in-situ spectral probe, the optical path including a window and a mirror.

12. The fiber-optic bundle of claim 1, further comprising a sampling head located at the sampling end, wherein the sampling head includes a fixture having a contoured inner wall having a shape that is complementary to a shape of an outer extent of the plurality of optical fibers for holding the plurality of optical fibers in a desired spatial arrangement during assembly of the fiber-optic bundle.

13. The fiber-optic bundle of claim 12, wherein the shape of the inner wall includes a plurality of elongate portions each having an arcuate cross sectional shape.

14. A system, comprising:
a soil probe;
a fiber-optic bundle according to claim 1 disposed in the soil probe; and
a mirror located in the soil probe adjacent the sampling end of the fiber-optic bundle.

15. The system of claim 14, wherein the first receiver fiber is configured to be connected to an infrared spectrometer and the second receiver fiber is configured to be connected to a visible light spectrometer, further wherein the mirror has a mirror surface that is positioned at an acute angle with respect to a central longitudinal axis of the sampling end of the fiber-optic bundle.

16. The system of claim 15, wherein a distance between a sampling end of the first receiver fiber and the mirror surface is substantially the same as a distance between a sampling end of the second receiver fiber and the mirror surface.

17. The system of claim 15, wherein a distance between a sampling end of the first receiver fiber and the mirror surface is less than a distance between a sampling end of the second receiver fiber and the mirror surface.

18. The system of claim 15, wherein a distance between a sampling end of the first receiver fiber and the mirror surface is greater than a distance between a sampling end of the second receiver fiber and the mirror surface.

19. The system of claim 15, further comprising an infrared (IR) spectrometer, a visible light (VIS) spectrometer, and a light source, further wherein the fiber-optic bundle includes a common portion that extends from the sampling end to a fiber leg junction and a plurality of legs that include a first leg that extends from the fiber leg junction to the IR spectrometer, a second leg that extends from the fiber leg junction to the VIS spectrometer, and a third leg that extends from the fiber leg junction to the light source, wherein a length of at least one of the plurality of legs is different than a length of the other legs.

20. The system of claim 19, wherein the third leg is connected to the light source by a connector, wherein the connector is a commercial off the shelf connector that has been modified to increase an internal diameter of the connector to maximize a total cross sectional area of core diameters of the plurality of illumination fibers.

* * * * *